United States Patent [19]
Godbole

[11] Patent Number: 6,054,603
[45] Date of Patent: Apr. 25, 2000

[54] ACRYLONITRILE RECOVERY PROCESS

[75] Inventor: Sanjay Purushottam Godbole, Solon, Ohio

[73] Assignee: The Standard Oil Company, Chicago, Ill.

[21] Appl. No.: 09/286,886

[22] Filed: Apr. 6, 1999

[51] Int. Cl.⁷ .................................................. C07C 255/00
[52] U.S. Cl. ............................................................ 558/466
[58] Field of Search ............................................. 558/466

[56] References Cited

U.S. PATENT DOCUMENTS

| | | | |
|---|---|---|---|
| 3,885,928 | 5/1975 | Wu | 55/85 |
| 4,234,510 | 11/1980 | Wu | 260/465.3 |
| 4,269,667 | 5/1981 | Landis | 558/466 |

*Primary Examiner*—Johann Richter
*Assistant Examiner*—Joseph Murray
*Attorney, Agent, or Firm*—Thomas E. Nemo; Stephen L. Hensley

[57] ABSTRACT

The process of the present invention comprises transporting a reactor effluent containing acrylonitrile/methacrylonitrile to a first column (quench) where the reactor effluent is cooled with a first aqueous stream, transporting the cooled effluent into an indirect contact cooler to condensed at least some of the cooled effluent to form a condensate comprising water and acrylonitrile/methacrylonitrile, transporting the remaining cooled gaseous effluent containing acrylonitrile/methacrylonitrile into a second column (absorber) where the cooled effluent is contacted with a second aqueous stream to absorb substantially all of the remaining acrylonitrile/methacrylonitrile into the second aqueous stream, transporting the second aqueous stream containing the acrylonitrile/methacrylonitrile to a first distillation column (recovery column) for separation of the crude acrylonitrile/methacrylonitrile from the second aqueous stream, and transporting the separated crude acrylonitrile/methacrylonitrile to a second distillation column (heads column) to remove at least some impurities from the crude acrylonitrile/methacrylonitrile, and transporting the partially purified acrylonitrile/methacrylonitrile to a third distillation column (product column) to further purify the acrylonitrile/methacrylonitrile, and recovering the purified acrylonitrile/methacrylonitrile, wherein the improvement comprises transporting the condensate formed in the indirect contact cooler to a decanter where the condensate is separated into an organic phase comprising acrylonitrile/methacrylonitrile, an aqueous phase and a vapor phase, and the organic phase is introduced into the recovery column without passing through the absorber column.

12 Claims, 1 Drawing Sheet

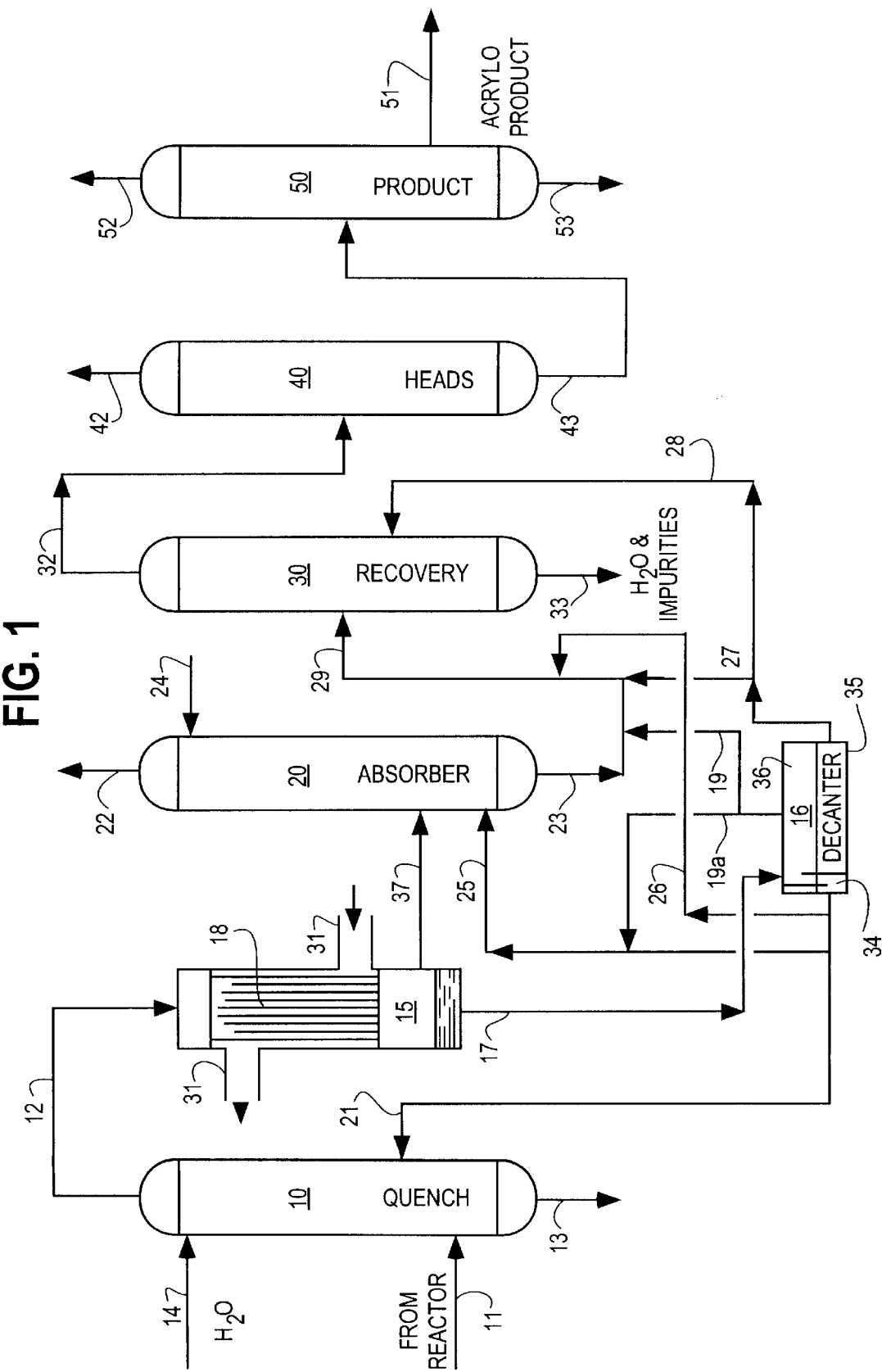

ACRYLONITRILE RECOVERY PROCESS

BACKGROUND OF THE INVENTION

The present invention is directed to an improved method for the manufacture of the corresponding nitrile produced during the ammoxidation of an unsaturated hydrocarbon selected from the group consisting of propylene and isobutylene. In particular, the process of the present invention is directed to an improvement in the recovery and purification process for acrylonitrile and methacrylonitrile.

In general, the recovery of acrylonitrile or methacrylonitrile produced by the ammoxidation of propylene or isobutylene on a commercial scale has been accomplished by contacting the hot reactor gaseous effluent containing the corresponding nitrile with an aqueous stream in a column (quench column) to cool the reactor effluent, passing the cooled gaseous stream containing the corresponding nitrile resulting to a second column (absorber column) where a second aqueous stream and the cooled gaseous stream are contacted in a counter-current flow and substantially all of the acrylonitrile or methacrylonitrile are absorbed into the second aqueous stream. This second aqueous stream containing substantially all of the acrylonitrile or methacrylonitrile is then subjected to further recovery and purification steps.

Typical recovery and purification procedures for acrylonitrile and methacrylonitrile are set forth in detail in U.S. Pat. Nos. 4,234,510 and 3,885,928 herein incorporated by reference. In addition, the above mentioned '510 patent discloses that indirect contact cooling of the gaseous effluents exiting the quench column prior to entry into the absorber column produces a considerable amount of nitrile condensation. This condensed liquid consisting mainly of the corresponding nitrile can be fed directly to the recovery and purification columns by passing the absorber column thereby decreasing capital and operating costs in the absorber operation. The use of an indirect contact cooling step can lead to the condensation of more than 50% of the corresponding nitrites which means that a majority of the corresponding nitrile may be fed directly into the recovery and purification column by passing the absorber operation.

SUMMARY OF THE INVENTION

It is the primary object of the present invention to provide an improved process for the recovery and purification of the corresponding nitrile produced during the ammoxidation of propylene and isobutylene.

It is another object of the present invention to provide an improved process for the manufacture of the corresponding nitrile produced during the ammoxidation of an unsaturated hydrocarbon selected from the group consisting of propylene and isobutylene.

Additional objects and advantages of the invention will be set forth in part in the description that follows, and, in part, will be obvious from the description or may be learned by practicing the invention. The objects and advantages of the invention may be realized and obtained by means of the instrumentalities and combinations particularly pointed out in the appended claims.

To achieve the foregoing objects and in accordance with the purpose of the present invention as embodied and broadly described herein, the process of the present invention comprises transporting a reactor effluent containing acrylonitrile/methacrylonitrile to a first column (quench) where the reactor effluent is cooled with a first aqueous stream, transporting the cooled effluent into an indirect contact cooler to condense at least some of the cooled effluent to form a condensate comprising water and acrylonitrile/methacrylonitrile, transporting the remaining cooled gaseous effluent containing acrylonitrile/methacrylonitrile into a second column (absorber) where the cooled effluent is contacted with a second aqueous stream to absorb substantially all of the remaining acrylonitrile/methacrylonitrile into the second aqueous stream, transporting the second aqueous stream containing the acrylonitrile/methacrylonitrile to a first distillation column (recovery column) for separation of the crude acrylonitrile/methacrylonitrile from the second aqueous stream, and transporting the separated crude acrylonitrile/methacrylonitrile to a second distillation column (heads column) to remove at least some impurities from the crude acrylonitrile/methacrylonitrile, and transporting the partially purified acrylonitrile/methacrylonitrile to a third distillation column (product column) to further purify the acrylonitrile/methacrylonitrile, and recovering the purified acrylonitrile/methacrylonitrile, wherein the improvement comprises transporting the condensate formed in the indirect contact cooler to a decanter where the condensate is separated into an organic phase comprising acrylonitrile/methacrylonitrile, an aqueous phase and a vapor phase, and the organic phase is introduced into the recovery column by passing the absorber column.

In a preferred embodiment of the present invention the organic phase is introduced directly into the recovery column.

In a further preferred embodiment of the present invention the organic phase is introduced into the recovery column at a point below the point in the recovery column where the second aqueous stream enters the recovery column.

In still another preferred embodiment of the present invention, the aqueous phase from the decanter is recycled into the absorber column.

In a still further preferred embodiment of the present invention the aqueous phase from the decanter is recycled into the quench column.

In another preferred embodiment of the present invention the organic phase is mixed with the second aqueous stream exiting the absorber column prior to entry into the recovery column.

In a further preferred embodiment of the present invention the vapor phase from the decanter is transported to the absorber column.

In still another preferred embodiment of the present invention the vapor phase from the decanter is transported to the recovery column.

In another aspect of the present invention, the process of recovering and purifying an unsaturated mononitrile selected from the group consisting of acrylonitrile and methacrylonitrile comprises quenching a reactor effluent containing the unsaturated mononitrile with a first aqueous stream, condensing at least a portion of the cooled effluent to form a condensate comprising water and at least a portion of the unsaturated mononitrile, separating the condensate into an aqueous phase, organic phase and vapor phase, transporting the remaining cooled gaseous effluent into an absorber column where the cooled effluent is contacted with a second aqueous stream to absorb substantially all of the remaining unsaturated mononitrile into the second aqueous stream, transporting the second aqueous stream containing the unsaturated mononitrile and at least the organic phase of the condensate to a first distillation column for separation of the crude unsaturated mononitrile from the second aqueous stream, and purifying the crude unsaturated mononitrile to obtain an unsaturated mononitrile substantially free of impurities.

In a preferred embodiment of this aspect of the present invention, the purification of the crude unsaturated mononitrile is performed by distillation.

In another preferred embodiment of this aspect of the present invention the unsaturated mononitrile is selected to be acrylonitrile.

The three phase decanter can be utilize to improve liquid and vapor traffic in the process of the present invention, in particular, in the recovery and purification of acrylonitrile or methacrylonitrile. The process of the present invention decreases the capital and operating expenses of the facility. Additionally, the introduction of an liquid organic phase to the recovery column from the three phase decanter as herein described reduces hydraulic loading and steam consumption in the recovery column resulting in savings of both capital and operating expenses. This invention is especially applicable to plants having a capacity of more than a million kilograms per year production.

The use of the three phase decanter of the process of the present invention to separate an organic stream highly concentrated in acrylonitrile or methacrylonitrile which can be fed in the recovery column feed along with the absorber bottoms has additional advantages over prior recovery and purification procedures. The aqueous phase from the three phase decanter concentrates peroxide impurities which can be directed to the absorber column. This provides an important way to remove the light peroxides in the absorber offgas as well as increase the concentration of acrylonitrile or methacrylonitrile in the recovery column liquid product stream. This permits a reduction of inhibitor usage and increases the acrylonitrile/methacrylonitile recovery efficiency. In the typical practice of the present invention, the aqueous phase in the decanter is usually about 80% water with substantially all of the peroxide impurities contained in this phase. The organic phase usually contains less than 10% water and substantially all of the acrylonitrile/methacrylonitrile.

BRIEF DESCRIPTION OF THE DRAWING

FIG. 1 shows a schematic representation of the process of the present invention as it applies to the recovery of acrylonitrile.

DETAILED DESCRIPTION OF THE INVENTION

The process of the present invention is directed to the purification of acrylonitrile or methacrylonitrile produced during the ammoxidation of propylene or isobutylene in a fluid bed in the presence of a catalyst. The fluid bed catalytic ammoxidation process for the manufacture of acrylonitrile and methacrylonitrile from propylene or isobutylene is well known and forms no part of the present invention. The details of the fluid bed ammoxidation process for acrylonitrile/methacrylonitrile may be found in U.S. Pat. No. 4,801,731 and U.K. Patent 1,265,770, herein incorporated by reference.

The process of the present invention entails separation of the condensed liquid from the indirect contact cooler into organic, aqueous and vapor phases using a three phase decanter. The compositions and relative quantities of the three phases can be altered by adjusting the temperature and pressure of the material fed to, or in, the three phase decanter. Methods for altering the temperature of the material fed to the three phase decanter are well know in the art and include, but are not limited to, direct and indirect heat exchangers, steam tracing, fireboxes, refrigeration units, and the addition of a tempering stream to raise or lower the temperature. Similar means may be used to adjust the temperature of the material in the three phase decanter. The operating pressure of the three phase decanter may also be adjusted to optimize operation. Typically, this may be effected by placing a pump in the liquid supply line to the decanter and a back pressure regulator on the effluent streams to increase pressure; by placing a pressure regulator or throttling device on the inlet stream, and withdrawing effluent streams to reduce pressure; by controlling the relative flow rate of the inlet stream to the effluent streams; or other methods known in the art. A maximum operating temperature of the three phase decanter is 75° F. (23.9° C.), preferably 60° F. (15.5° C.), more preferably 55° F. (12.8° C.). A minimum operating temperature of the three phase decanter is 35° F., preferably 33.8° F. (1° C.), more preferably 35.6° F. (2° C.), and most preferably 53.6° F. (12° C.). A maximum operating pressure of the three phase decanter is about 25 psia, preferably about 20 psia, and most preferably about 15 psia. Alternately, the operating temperature and operating pressure of the three phase decanter may be permitted to vary, dependent upon the process units upstream and downstream of the decanter. At least a portion of the condensed liquid from the indirect contact cooler is directed to the three phase decanter. Preferably, the majority of the condensed liquid from the indirect contact cooler is directly fed to the three phase decanter. Most preferably, all of the condensed liquid from the indirect contact cooler is directly fed to the three phase decanter.

In typical acrylonitrile or methacrylonitrile process, a direct contact cooling of the reactor effluent is followed by the condensation of at least some of the acrylonitrile or methacrylonitrile in an indirect contact cooler. The amount of unsaturated nitrile that is condensed in the indirect contact cooler may vary from a small amount to essentially all of the nitrile. In a preferred practice of the invention about 10 to about 90% of the nitrile fed to the indirect contact cooler is condensed, with the condensation of about 25 to 75% being especially economical.

The amount of acrylonitrile or methacrylonitrile condensed in the present invention and directed to the three phase decanter is broadly determined by the temperature and pressure conditions of the indirect cooler. Other variables such as the presence of azeotropic agents and entrainment of the nitrites in the gas flow remain relatively stable under normal operating conditions.

A primary variable controlling the condensation is the temperature. As the temperature is decreased, the amount of acrylonitrile or methacrylonitrile condensed is increased. Of course, the decrease of the temperature to very low levels required substantial indirect contact cooling. Determination of the desired temperature of operation is essentially a trade-off between the amount of nitrile condensed and the cost of the indirect cooling.

The optimum strategy, of course, is to condense as much acrylonitrile or methacrylonitrile as possible at minimum cost. The most economical operation will depend on the availability and cost of cooling capacity, capital and operating cost calculations and a number of other factors.

The present invention will now be described in detail with reference to the accompanying drawing.

Referring to FIG. 1, the reactor effluent from the ammoxidation of propylene (reactor not shown) is fed through conduit 11 into the direct contact cooler (quench column) 10. In quench column 10 water is fed through line 14 to contact the reactor effluent to cool the effluent to a temperature of about 40° C. to about 100° C. Polymers, ammonium sulfate and other condensible and soluble materials are passed through line 13 to a waste treatment system or recycle (not shown). The temperature and pressure utilized are not critical to the practice of the process of the present invention but should be maintained in such a manner that little or none of the acrylonitrile is condensed. These conditions can readily be determined by one having ordinary skill in the art The gaseous effluent from the direct contact cooler 10 containing substantially all the acrylonitrile is passed as an overhead and is fed through line 12 into indirect contact cooler 15. Indirect contact cooler 15 contains chambers 18, such as tubes, and the effluent is fed through chambers 18. The inner surface of the chambers 18 are cooled by a flow of coolant (e.g. water) via line 31 on the outer surface of chambers 18. Contact between the cooled inner surface of chambers 18 and the hot effluent gas cools the effluent gas to condense at least some of the acrylonitrile in the bottom of indirect contact cooler 15.

The uncondensed effluent from indirect contact cooler 15 passes through line 37 to column 20 (absorber) where the majority of the remaining acrylonitrile is scrubbed from the gas by water flowing through conduit 24. The water containing acrylonitrile is passed through line 23 to line 29 into recovery column 30. The gases not dissolved in the water in absorber 20 pass overhead through conduit 22.

The condensed liquid from indirect contact cooler 15 comprising acrylonitrile and water is transferred through conduit 17 to a three phase decanter 16. The three phase decanter 16 separates the liquid into an aqueous phase 34, an organic phase 35, and a vapor phase 36. The aqueous phase 34 may be fed back to absorber 20 via line 25, or back to quench 10 via line 21 or combined via line 26 with the water containing acrylonitrile from the absorber 20 and fed to the recovery column 30 via line 29. The vapor phase 36 may also be combined via line 19 with the water containing acrylonitrile exiting absorber 20 and fed to the recovery column 30 or via line 19a to absorber 20. The organic phase 35 may be combined with the water containing acrylonitrile from absorber 20 and the vapor phase 36 from the three phase decanter 16 and fed together to recovery column 30 via line 29.

In an alternate configuration, the organic phase 35 may be fed directly to recovery column 30 via line 28 at a point below the location of line 29. Acrylonitrile is recovered from column 30 as an overhead and transferred to heads column 40 via line 32 for further purification (distillation). The acrylonitrile is then transferred to product column 50 via line 43 for a final distillation and product acrylonitrile is recovered as a sidestream from column 50 via line 51.

What is claimed as the invention is:

1. The process of recovering and purifying an unsaturated mononitrile selected from the group consisting of acrylonitrile and methacrylonitrile comprises transporting a reactor effluent containing the unsaturated mononitrile to a first column where the reactor effluent is cooled with a first aqueous stream, transporting the cooled effluent into an indirect contact cooler to condense at least some of the cooled effluent to form a condensate comprising water and at least a portion of the unsaturated mononitrile, transporting the remaining cooled gaseous effluent containing the remaining unsaturated mononitrile into a second column where the cooled effluent is contacted with a second aqueous stream to absorb substantially all of the remaining unsaturated mononitrile into the second aqueous stream, transporting the second aqueous stream containing the unsaturated mononitrile to a first distillation column for separation of the crude unsaturated mononitrile from the second aqueous stream, and transporting the separated crude unsaturated mononitrile to a second distillation column to remove at least some impurities from the crude unsaturated mononitrile, and transporting the partially purified unsaturated mononitrile to a third distillation column to further purify the unsaturated mononitrile, and recovering the purified unsaturated mononitrile, wherein the improvement comprises transporting the condensate formed in the indirect contact cooler to a decanter where the condensate is separated into an organic phase comprising unsaturated mononitrile, an aqueous phase and a vapor phase, and introducing the organic phase into the first distillation column without passing through the second column.

2. The process of claim 1 wherein the organic phase is introduced directly into the first distillation column.

3. The process of claim 2 wherein the organic phase is introduced into the recovery column at a point below the point in the first distillation column where the second aqueous stream enters the first distillation column.

4. The process of claim 1 wherein the aqueous phase from the decanter is recycled into the second column.

5. The process of claim 1 wherein the aqueous phase from the decanter is recycled into the first column.

6. The process of claim 1 wherein the organic phase is mixed with the second aqueous stream exiting the second column prior to entry into the recovery column.

7. The process of claim 1 wherein the vapor phase from the decanter is transported to the second column.

8. The process of claim 1 wherein the vapor phase from the decanter is transported to the first distillation column.

9. The process of recovering and purifying an unsaturated mononitrile selected from the group consisting of acrylonitrile and methacrylonitrile comprises quenching a reactor effluent containing the unsaturated mononitrile with a first aqueous stream, condensing at least a portion of the cooled effluent to form a condensate comprising water and at least a portion of the unsaturated mononitrile, separating the condensate into an aqueous phase, organic phase and vapor phase, transporting the remaining cooled gaseous effluent into an absorber column where the cooled effluent is contacted with a second aqueous stream to absorb substantially all of the remaining unsaturated mononitrile into the second aqueous stream, transporting the second aqueous stream containing the unsaturated mononitrile and at least the organic phase of the condensate to a first distillation column for separation of the crude unsaturated mononitrile from the second aqueous stream, and purifying the crude unsaturated mononitrile to obtain an unsaturated mononitrile substantially free of impurities.

10. The process of claim 9 wherein the purification of the crude unsaturated mononitrile is performed by distillation.

11. The process of claim 9 wherein the unsaturated mononitrile is selected to be acrylonitrile.

12. The process of claim 1 wherein the unsaturated mononitrile is selected to be acrylonitrile.

* * * * *

UNITED STATES PATENT AND TRADEMARK OFFICE
CERTIFICATE OF CORRECTION

PATENT NO. : 6,054,603
DATED : April 25, 2000
INVENTOR(S) : Sanjay Purushottam Godbole It is certified that error appears in the above-identified patent and that said Letters Patent is hereby corrected as shown below:

| Col. | Line | |
|---|---|---|
| 1 | 1 | "ACRYLONITRILE RECOVERY PROCESS"<br><br>should read:<br>"IMPROVED ACRYLONITRILE RECOVERY PROCESS" |
| 1 | 40 | "corresponding nitrites"<br><br>should read:<br>"corresponding nitriles" |
| 4 | 50 | "the nitrites in the gas"<br><br>should read:<br>"the nitriles in the gas" |

Signed and Sealed this

Tenth Day of April, 2001

Attest:

NICHOLAS P. GODICI

Attesting Officer

Acting Director of the United States Patent and Trademark Office